United States Patent [19]
Ennis, III et al.

[11] Patent Number: 5,344,409
[45] Date of Patent: Sep. 6, 1994

[54] SYRINGE LATCH

[75] Inventors: James F. Ennis, III, Preston, Conn.; Sylvan L. Johnson, Woodville, Wis.

[73] Assignee: Genesis Industries Inc., Elmwood, Wis.

[21] Appl. No.: 75,890

[22] Filed: Jun. 14, 1993

[51] Int. Cl.⁵ ............................................. A61M 5/00
[52] U.S. Cl. .................................. 604/210; 604/187; 604/208
[58] Field of Search ............... 604/187, 207, 208, 209, 604/210, 218

[56] References Cited
U.S. PATENT DOCUMENTS 3,563,240  2/1971  Silver .
4,153,056  5/1979  Silver et al. ........................ 604/211
4,275,729  6/1981  Silver et al. .
4,874,385  10/1989  Moran et al. ....................... 604/210

Primary Examiner—C. Fred Rosenbaum
Assistant Examiner—N. Kent Gring
Attorney, Agent, or Firm—Edward H. Loveman

[57] ABSTRACT

A syringe for controlling the amount of material or medical fluid in a syringe body which is expelled therefrom upon depression of a plunger in the syringe body. The syringe includes a syringe body having a chamber and a discharge end portion and an open opposite end portion, with a plunger received in the syringe body. A measuring ring having an inner thread in mesh with an outer thread on the plunger, with latch means for setting and holding the measuring ring and plunger and thus, permit an exact volume to be expelled from said chamber.

6 Claims, 2 Drawing Sheets

SYRINGE LATCH

The invention generally relates to a syringe and in particular, the invention relates to a syringe having a plunger and barrel with a ring engaged on the plunger for dispensing controlled amounts of a fluid in the barrel.

BACKGROUND OF THE INVENTION

The prior art syringe is described in U.S. Pat. No. 4,153,056, issued May 8, 1979. A related patent is U.S. Pat. No. 3,563,240, issued Feb. 17, 1971. The prior art syringe includes a cylinder having a chamber and having a cannula with a core at a first end thereof, and having an open second end thereof, the cylinder has exterior finger flanges disposed adjacent the open second end, a plunger having a piston head with a ring seal disposed in the cylinder for sealing the chamber at a first end of the plunger and having a stem with four ribs in a cruciform shape fixedly connected to the piston head and having a thumb engaging flange fixedly connected to the four ribs at a second end of the plunger, each of the ribs having an Outer edge with a set of spaced notches forming an exterior thread, and a measuring ring having an interior thread in mesh with the exterior thread notches formed on the stem flanges for measuring and setting a selective volume in the chamber and bore for holding a selective volume of medical fluid. One problem with the prior art syringe is that it is sometimes difficult for operator to set the measuring ring at a selective angle relative to the plunger for setting an exact desired volume in the chamber and core.

SUMMARY OF THE INVENTION

According to the present invention, a syringe is provided with a cylinder having a chamber and a cannula with a bore at a first end thereof and having an open second end thereof, the cylinder having exterior finger flanges disposed adjacent to the open second end, a plunger having a piston head with a ring seal disposed in the cylinder for sealing the chamber at a first end of the plunger and having a stem with first and second and third and fourth ribs in a given cross shape fixedly connected to the piston head and having a thumb engaging flange fixedly connected to the four ribs. At a second end of the plunger, the ribs have respective outer edges with first, second, third and fourth sets of notches forming an exterior thread, and a measuring ring having an interior thread in mesh with the exterior thread notches formed on the ribs permitting a predetermined volume of fluid in the chamber to be dispensed by the plunger. The interior thread on the ring has a pair of detents projecting radially inwardly of the first, second, third and fourth sets of rib thread notches, each of which have minor thread diameters, wherein the first, second and third sets of stem flange thread notches have a uniform selective minor thread diameter for allowing clearances in a radial direction from the pair of detents, and wherein the fourth set of rib thread notches have a selective minor thread diameter which is larger than the uniform selective minor thread diameter whereby the pair of detents do not have any clearance in a radial direction from the pair of detents when adjacent thereto, so that the measuring ring is latched to the plunger upon disposition of the pair of detents on opposite sides of the fourth set of rib thread notches.

By using the measuring ring thread detents an operator can set a desired volume of fluid which may be expelled from the syringe. The angle of the threads on the ribs and the measuring ring may be changed to permit a change in the volume to be expelled from the syringe for each revolution of the measuring ring.

A principal object of the present invention is to provide a syringe which will expel predetermined accurate volume of fluid for each revolution-of the measuring ring.

One object of the present invention is to avoid the difficulty for an operator in setting the measuring ring at a selective angle relative to the plunger or setting exactly a desired volume in the chamber and the bore for holding a selective volume of medical fluid.

These and other objects and many of the attendant advantages of this invention will be readily appreciated as the same becomes better understood by reference to the following detailed description when considered in connection with the accompanying drawings in which:

DESCRIPTION OF THE PREFERRED EMBODIMENT

Figure 1:
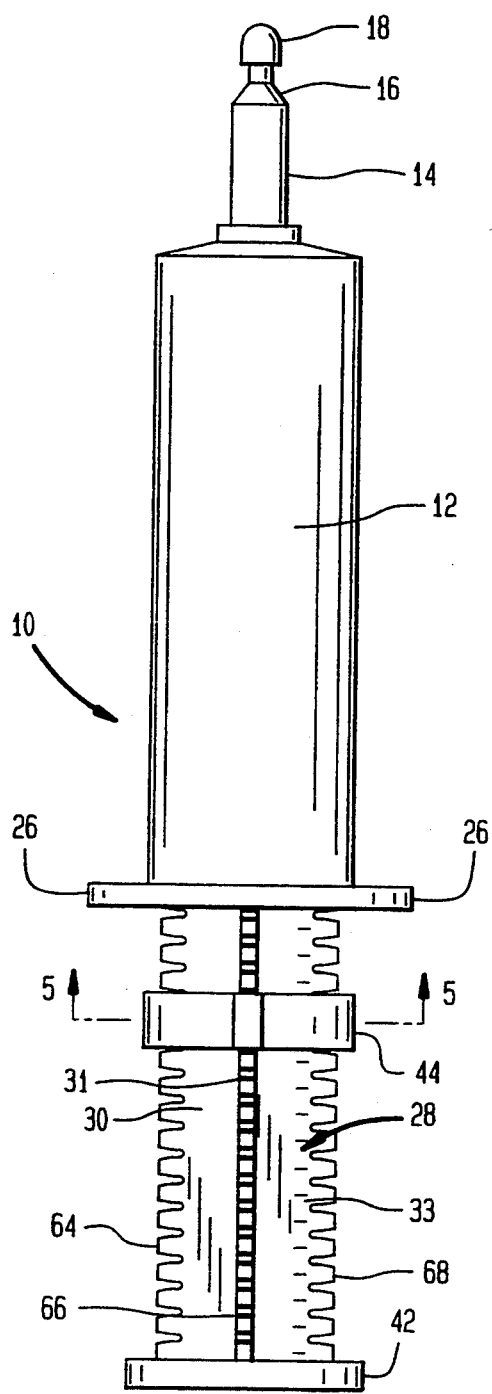
FIG. 1 is an elevational view of the syringe according to the invention.
Figure 2:
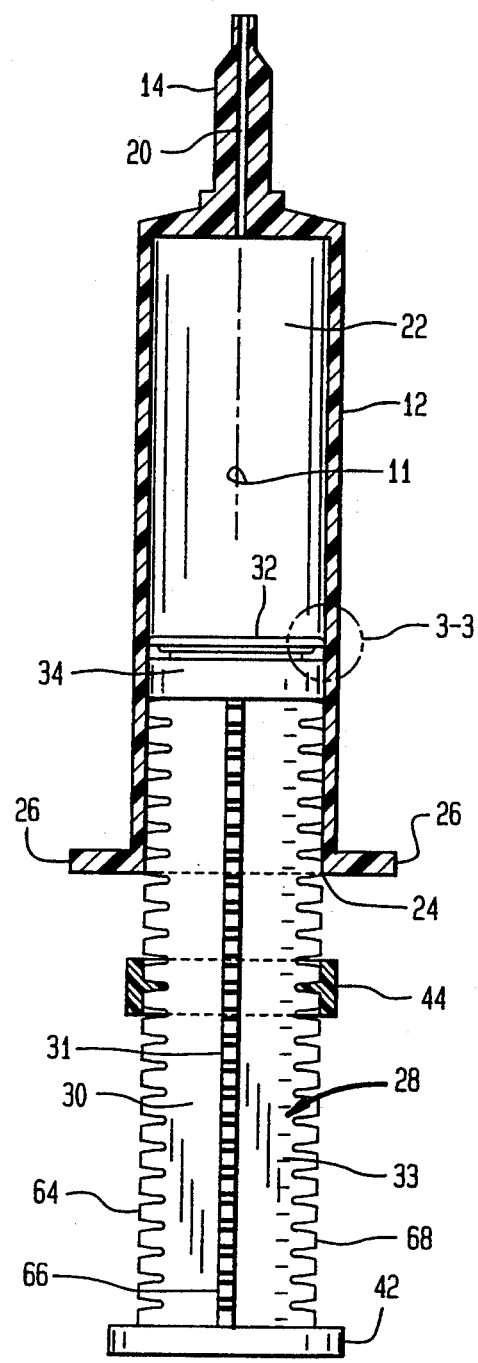
FIG. 2 is a longitudinal sectional view of the syringe shown in FIG. 1.

Referring now to the drawings wherein like reference characters designate like or corresponding parts throughout, there is illustrated in FIG. 1, a variable dosage syringe generally designated by reference numeral 10 which has an axis 11 and includes a hollow syringe body or cylinder 12 formed of a synthetic plastic material, or the like, and includes an elongated tubular cannula 14 having a tapered end portion 16 that is electively closed by a removable cap 18. As seen in FIG. 2, the cannula 14 has a bore 20 formed therein which communicates with an internal chamber 22 of the syringe body 12. This chamber is adapted to receive a pharmaceutical preparation or the like which is intended to be dispensed from the chamber 22 through the bore 20 of the cannula 14.

The chamber 22 has a uniform diameter from one end to the other and is open at an end 24 thereof opposite the cannula 14. Laterally extending handles or finger flanges 26 are provided adjacent this end of the syringe body 12 in a conventional manner.

The medicament is expelled from the chamber 22 through the bore 20 by a plunger 28 having a stem portion or an integral body formed of a plurality of radially extending ribs 29, 30, 31, 33, in a cruciform array. The plunger 28 has a first or inner end portion 32 which includes an integral or snap on seal piston 34 formed thereon and adapted to be inserted through an open end 24 of the syringe body 12. The opposite end of the plunger 28 has an integral palm or thumb engaging base or flange 42 formed thereon in a conventional manner.

Figure 3:
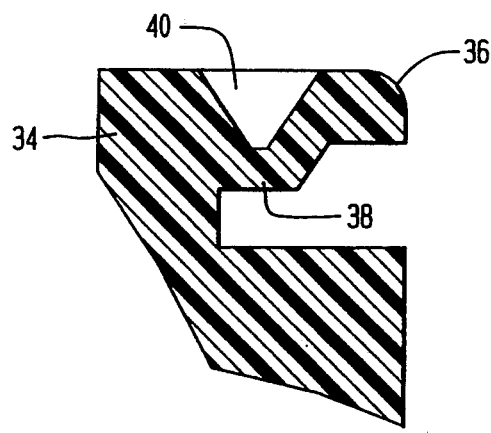
FIG. 3 is an enlarged partial sectional view of an edge portion of the plunger piston and seal arrangement of the present invention.
Figure 4:
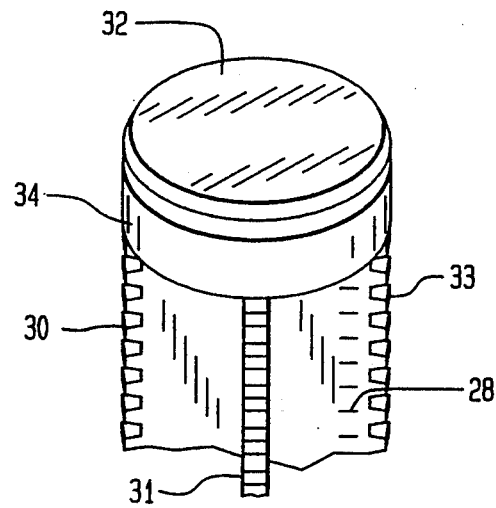
FIG. 4 is a partial perspective view illustrating the threaded stem of the plungers.

The piston 34 includes an integral annular seal or flange 36 surrounding the piston 34 and having a diameter which is greater than the maximum diameter of the ribs 29, 30, 31, 33 of the plunger 28. As shown in FIG. 3, the flange 36 is connected to the piston 34 by an integral annular web 38 which is formed in the piston 34 by an annular V-shaped notch 40, so that the web 38 has a reduced thickness as compared to the flange 36 and is flexible, to permit the flange 36 to serve as a wiping seal along the interior surface of the syringe body 12.

A plunger limiting nut or ring 44 is provided on the plunger 28. The ring may be rotated to be properly located along the length of the plunger so that to permit a proper dosage of the material in the chamber to expelled through cannula 14. Thus by adjusting the distance of the annular ring 44 from the finger flanges 26, more or less material from the syringe 10 can be expelled.

Figure 5:
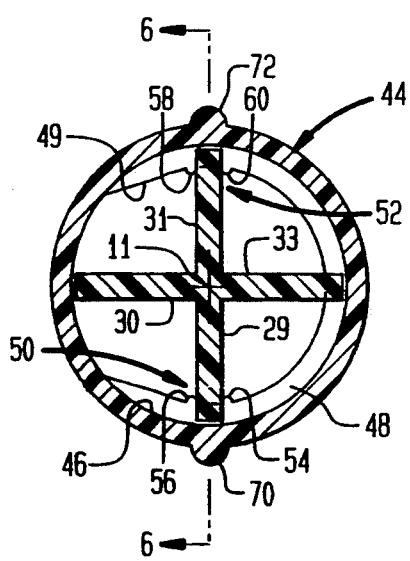
FIG. 5 is a sectional view as taken along line 5—5 of FIG. 1.

As shown in FIG. 5, the ring 44 has an inner surface 46, which has a horseshoe shaped segmental rib or inner thread 48, that has an inner face 49. The thread 48 has a first latch 50 and a second latch 52, which are located 180 degrees apart. The latch 50 has a first and second detent or projection 54,56. The latch 52 also has a third and fourth detent or projection 58, 60. The detents 54, 56, 58, 60 are made of a resilient conventional plastic material and each extends from the inner face 49 in a radially inward direction. The detents 54, 56, and 58, 60 respectively are disposed on the peripherally opposite sides of the ribs 29 and 31, in the latched condition as shown in FIG. 5.

Figure 6:
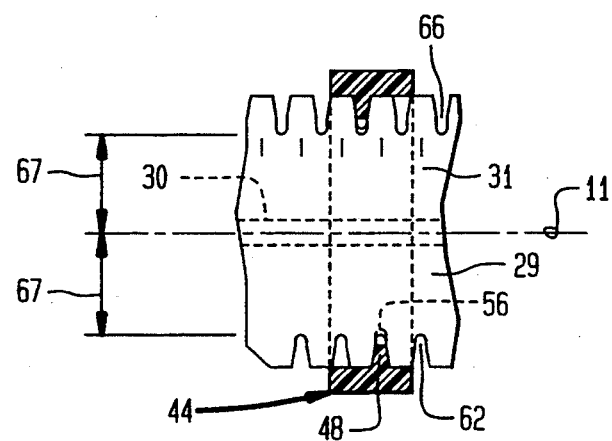
FIG. 6 is a sectional view as taken along line 6—6 of FIG. 5.

As illustrated in FIG. 2 and FIG. 6, the flanges 29, 30, 31, 33 have along their outer edges respective sets of axially spaced notches 62, 64, 66, 68, which receive the inner thread 48. The three sets of notches 64, 66, 68, of the respective fibs 31, 32, 33 have a uniform similar minor thread diameter and radius 67. The fourth set of notches 62 of the rib 29 has a minor thread diameter and radius 69 which is slightly larger than the uniform minor thread diameter and its radius 67. Thus, the latch 50 or 52 can only engage the plunger 28 on the fourth set of notches 62 of the stem flange 29. It should be noted that the minor thread diameter and radius extends to the valley or root of the notch and in a typical example, the axial width of each of the notches 62, 64, 66, 68 is slightly larger than the corresponding axial width of each of the detents 54, 56, 58, 60 and also larger than the corresponding axial width of the inner thread 48. Thus, the tip portions of the detents 54, 56, or 58, 60 act to latch or hold the sides of one notch in the set of notches 62, adjacent to the root of the notch.

In this embodiment 10, the ring 44 has an outer surface with a pair of ribs 70,72. Ribs 70, 72 which are respectively disposed radially outwardly of the latches 50, 52 in order to aid the operator to line up the ring 44 with the contacting flange 29 of the plunger 28. In an alternate embodiment (not shown), painted markings or raised arrows may be used in place of the ribs 70, 72. In another alternate embodiment (not illustrated), the ring 44 may have a rough finish or rippled finish in place of the smooth finish on its outer surface; or the ring 44 may have a plurality of equally angularly spaced ribs on its outer surface, in addition to the ribs 70, 72 which have a painted marking.

In this embodiment ring 44 is adjustable relative to the ribs 29, 30, 31, 33 by an angular displacement of the ring 44, and a half turn of the ring 44 may provide a two cubic centimeters (cc) volume change or dose in the chamber 22, including the bore 20. In alternate embodiments, other doses may be accommodated by changing the pitch angle of the thread such that a single turn of the ring 44 can produce one cc or another pitch angle of the thread would produce 3 cc with a single turn of the ring 44. The advantage of the syringe 10 is that the operator avoids the difficulty in setting measuring ring 44 at a selective angle relative to the plunger 28, for exactly setting a desired volume in the chamber.

It should be understood that the foregoing relates only to a limited number of preferred embodiments of the invention which have been by way of example only, and that is intended to cover all change and modifications of the examples of the invention herein chosen for the purposes of the disclosure which do not constitute departures from the spirit and scope of the invention.

What is claimed:

1. A syringe comprising:
   a hollow syringe body having a discharge end portion and an open opposite end portion;
   a plunger slidable in said syringe body through said open end portions thereof, said plunger having a first end portion located within said syringe body including a seal formed thereon between said plunger and the interior of said syringe body;
   a length adjusting member engaged with said plunger outside of said syringe body to variably limit operating travel of said plunger in said syringe body thereby to control the volume of a fluid in the syringe body expelled therefrom upon depression of said plunger into said syringe body;
   said length adjusting member comprising a threaded nut having an internally disposed latch means for latching said nut to said plunger at a selective angle of displacement of said nut relative to said plunger;
   wherein said threaded nut comprises a one piece collar having an internal thread formed thereof, and said internal latch means comprising at least one pair of latch detents, said latch detents being made of a flexible material, and wherein said plunger includes a piston head and a stem having a plurality of ribs with a set of notches at an outer edge of each rib forming an exterior thread which mates with said internal thread of said collar; and
   wherein one of said ribs has a notch minor thread diameter which is larger than a notch uniform minor thread diameter of the other ribs for latching said collar to said plunger.

2. A syringe comprising:
   a hollow syringe body having a discharge end portion and an open opposite end portion and defining a chamber therein adapted to contain a material to be dispensed through said discharge end portion;
   a plunger slidable in said chamber through said open end portion of said syringe body, said plunger having first and second opposite end portions with said first end portion located in said chamber and having a transverse piston formed thereon, said piston including a main body portion, and an integral peripheral flange whose peripheral configuration is generally complementary to the internal configuration of said chamber to form a seal against the inner surface if said syringe body and an integral flexible peripheral web connecting said flange to said main body portion;

said plunger including a stem portion extending between said piston and said second plunger end portion having means thereon for defining a screw thereof; and a length adjusting member threadably engaged with said stem of said plunger outside of said syringe body and including a means for latching said length adjusting member to said plunger at a selective angle of angular displacement of said length adjusting member relative to said plunger, whereby said length adjusting member permits a predetermined volume of said material to be dispensed from said syringe and wherein said means for latching said length adjusting member comprises a measuring ring having an interior thread, and at least one pair of detents mounted on said interior thread for latching said measuring ring to said plunger at each one-half turn of said measuring ring, whereby said predetermined volume is measured by each detent said measuring ring passes when it is rotated.

3. A syringe comprising:

a hollow syringe body having a discharge end portion and an open opposite end portion and defining a chamber therein adapted to contain a material to be dispensed through said discharge end portion;

a plunger slidable in said chamber through said open end portion of said syringe body, said plunger having first and second opposite end portions with said first end portion located in said chamber and having a transverse piston formed thereon, said piston including a main body portion, and an integral peripheral flange whose peripheral configuration is generally complementary to the internal configuration of said chamber to form a seal against the inner surface if said syringe body and an integral flexible peripheral web connecting said flange to said main body portion;

said plunger including a stem portion extending between said piston and said second plunger end portion having means thereon for defining a screw thread;

a length adjusting means threadably engaged with said stem of said plunger outside of said syringe body and including a means for automatically latching said length adjusting member to said stem portion upon a relative angular displacement of said length adjusting member relative to said stem portion, such that said length adjusting member permits a predetermined volume of said material to be dispensed from said syringe; and said automatic latching means comprising a measuring ring having an interior thread, and at least one pair of detents disposed 180 degrees apart and mounted on said interior thread for latching said measuring ring to said plunger at each one-half turn of said measuring ring whereby said predetermined volume is measured by each detent said measuring ring passes when it is rotated.

4. A syringe comprising:

a hollow syringe body having a discharge end portion and a plunger slidable in said syringe body; and a length adjusting member engaged with said plunger outside of the syringe body to variably limit operating travel of said plunger in said syringe body, thereby to control an amount of material in said syringe body expelled therefrom upon depression of said plunger in said syringe body;

said length adjusting member comprising an internally threaded nut including a first latch and a second latch disposed 180 degrees apart and mounted on an interior thread of said first latch having first and second detents said second latch having third and fourth detents, said plunger having a first, a second, a third and fourth stem ribs, said stem flanges having respective first, second, third and fourth sets of notches, said first, second, and third sets of notches having a similar uniform minor thread diameter, said fourth set of notches having a minor thread diameter which is larger than said uniform minor thread diameter for latching a pair of detents when opposite thereto.

5. A syringe comprising:

a hollow syringe body having a discharge end portion, a plunger slidable in said syringe body; and a length adjusting member engaged with said plunger outside of said syringe body to variably limit operating travel of said plunger in said syringe body, thereby to control the amount of a material in said syringe body expelled therefrom upon depression of said plunger into said syringe body;

said length adjusting member comprising a one piece collar having an internal thread formed thereon, said internal thread of said collar having a first latch and a second latch disposed 180 degrees apart, said first latch having first and second detents, said second latch having third and fourth detents, said plunger having four ribs with respective first, second, third and fourth sets of notches, said first, second, and third sets of notches having a uniform minor thread diameter and a respective radius, said fourths set of notches having a larger minor thread diameter and a radius which are larger than the uniform minor thread diameter and its corresponding radius, and said collar having an outer surface having a pair of ribs disposed 180 degrees apart and disposed radially outwardly of said respective first and second latches.

6. A syringe comprising:

a cylinder having a chamber with a longitudinal axis;

said cylinder having a cannula with a bore at a first end of said cylinder; said cylinder having an open second end;

said cylinder having exterior finger flanges disposed adjacent to said open second end;

a plunger having a piston head with a ring seal disposed in said cylinder for sealing said chamber at a first end of said plunger;

said plunger having a stem with first and second and third and fourth ribs disposed in a cross shape and fixedly connected to said piston head;

said plunger having a thumb engaging flange fixedly connected to said four ribs at a at a second end of said plunger;

said ribs having respective outer edges with respective first and second and third and fourth sets of rib notches thereby forming an exterior thread;

a measuring ring having an interior thread in mesh with said exterior thread rib notches formed on said ribs for permitting a selective volume of a fluid in said chamber to be dispensed therefrom when said plunger is depressed in said cylinder;

said interior thread having at least one pair of detents projecting radially inwardly;

said first, second and third sets of rib notches having a similar uniform selective minor thread diameter; and said fourth set of rib notches having a minor thread diameter which is larger than said uniform minor thread diameter for latching said pair of detents with said fourth set of rib notches upon a selective angle of displacement of said measuring ring relative to said plunger.

* * * * *